United States Patent
Gscheidmeier et al.

(10) Patent No.: US 6,266,387 B1
(45) Date of Patent: Jul. 24, 2001

(54) COMMAND SEQUENCER FOR A CT IMAGING SYSTEM

(75) Inventors: Jason M. Gscheidmeier, Franklin; Kenneth G. Dunahee, Muskego, both of WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 09/397,553

(22) Filed: Sep. 16, 1999

(51) Int. Cl.$^7$ ........................................................ A61B 6/03

(52) U.S. Cl. ................................ 378/4; 378/116; 378/901

(58) Field of Search ........................... 378/4, 114, 115, 378/116, 901

(56) References Cited

U.S. PATENT DOCUMENTS

| | | | |
|---|---|---|---|
| 4,300,096 | * 11/1981 | Harrison et al. | 324/309 |
| 4,694,404 | * 9/1987 | Meagher | 345/421 |
| 5,056,006 | * 10/1991 | Acharya et al. | 711/147 |
| 5,417,218 | * 5/1995 | Spivey et al. | 600/484 |

* cited by examiner

Primary Examiner—David V. Bruce
(74) Attorney, Agent, or Firm—Quarles & Brady, LLP; Christian G. Cabou

(57) ABSTRACT

A CT imaging system employs a command sequencer to control the operation of the x-ray source and the data acquisition system. The command sequencer stores a set of commands in a FIFO memory that are read out in sequence to perform a scan. Each command contains a count field which indicates how long it is active and other fields enable different clock sources to be selected, enable commands to be repeated and enable command execution to be halted.

16 Claims, 2 Drawing Sheets

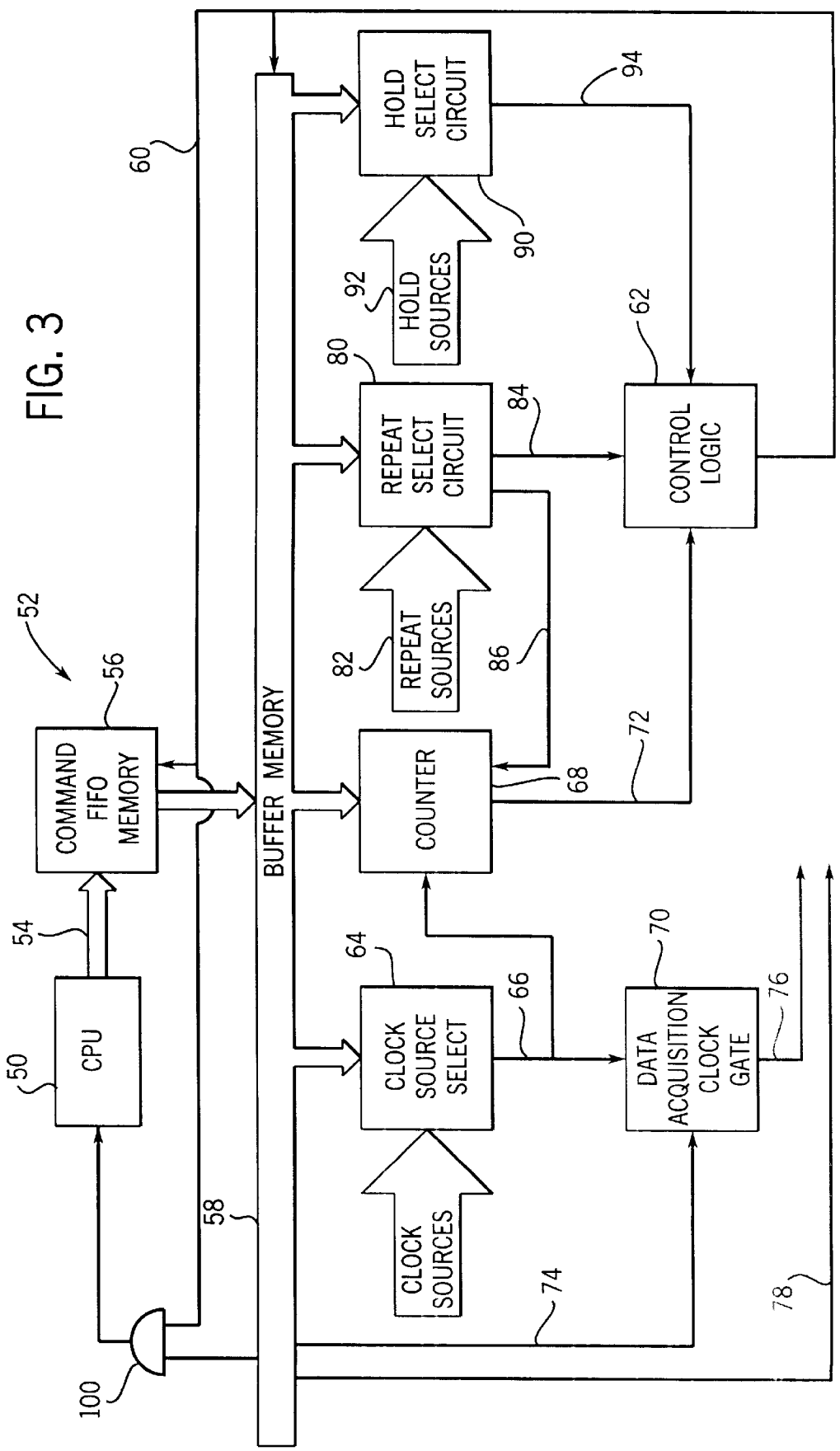

COMMAND SEQUENCER FOR A CT IMAGING SYSTEM

BACKGROUND OF THE INVENTION

The present invention relates to computed tomography (CT) imaging apparatus; and more particularly, to the control of the x-ray source and data acquisition system during a scan.

In a current computed tomography system, an x-ray source projects a fan-shaped beam which is collimated to lie within an X-Y plane of a Cartesian coordinate system, termed the "imaging plane". The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately and digitized by a data acquisition system to produce the transmission profile.

The x-ray source and detector array in a conventional CT system are rotated on a gantry within the imaging plane and around the object so that the angle at which the x-ray beam intersects the object constantly changes during a scan. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

The operation of the x-ray generator and the acquisition system during a scan is controlled by a programmed computer. The operator prescribes a scan and in response to the prescribed scan parameters, the computer executes a program which controls the various elements of the CT imaging system to carry out the scan. The computer produces an output signal that repeatedly turns the x-ray source on and off as the gantry is rotated. It also produces an output signal that directs the data acquisition system to repeatedly sample the signals produced by the radiation detectors during the scan.

Modern CT imaging systems are called upon to conduct many different types of scans. For each of these different scans specific software is developed to operate system elements such as the x-ray source and the data acquisition system. Such software has become very complex and difficult to develop. This results from the increasingly complex and sophisticated scans that have been developed and from the increased demand for high speed scans.

SUMMARY OF THE INVENTION

The present invention is a command sequence for a CT imaging system which receives a series of commands from a programmed processor and which controls the operation of an x-ray source and the operation of a data acquisition system to carry out a prescribed scan. More particularly, the command sequence includes: a command FIFO memory which stores a series of commands required to carry out a prescribed scan; a counter responsive to a count field in each command to establish the duration of each command read from the FIFO memory; an x-ray command line responsive to an x-ray enable bit in each command to energize or de-energize an x-ray source during the duration of the command; a data acquisition clock gate responsive to a data acquisition enable bit in each command to produce a data acquisition signal during the duration of the command; and control logic for reading out the next command in the command FIFO memory at the completion of each command. Once the series of commands are stored in the FIFO memory, the programmed processor is free to carry out other functions during the scan. The command sequencer operates autonomously to produce the signals necessary to operate the x-ray source and data acquisition system during the scan.

BRIEF DESCRIPTION OF THE DRAWINGS

FIG. 3 is a block schematic diagram of a command sequencer which forms part of the CT imaging system of FIG. 2.

DESCRIPTION OF THE PREFERRED EMBODIMENT

Figure 1:
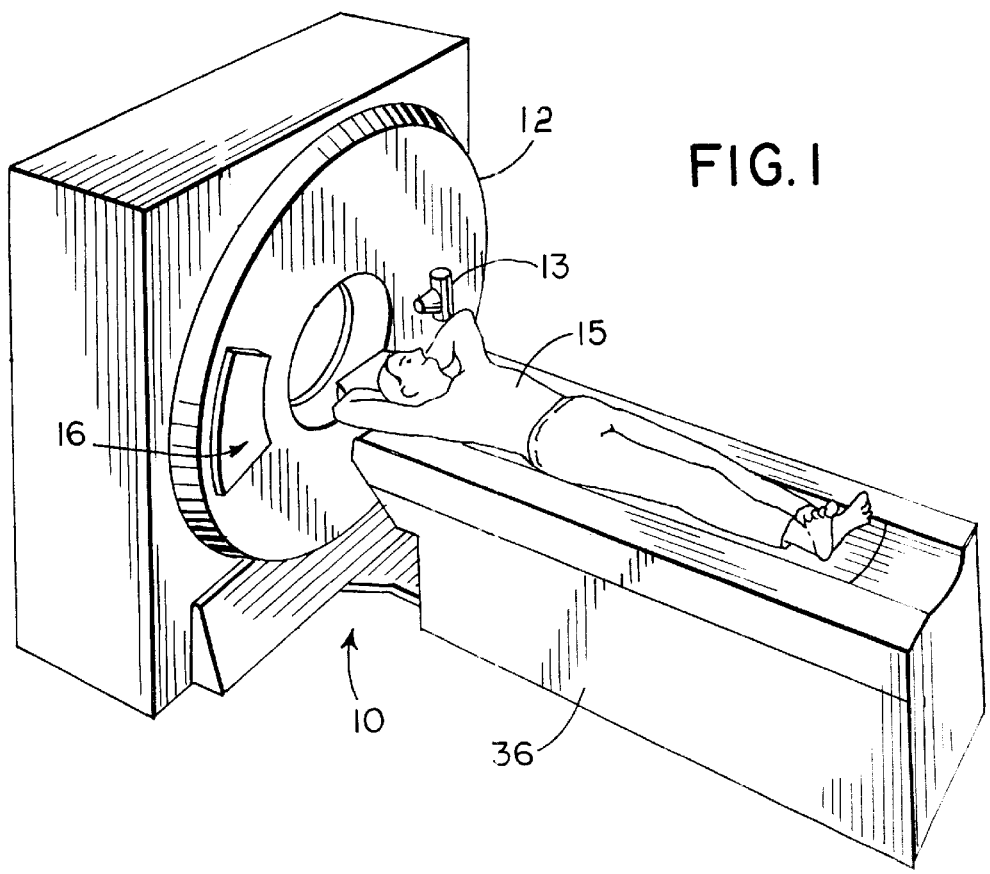
FIG. 1 is a pictorial view of a CT imaging system in which the present invention may be employed.
Figure 2:
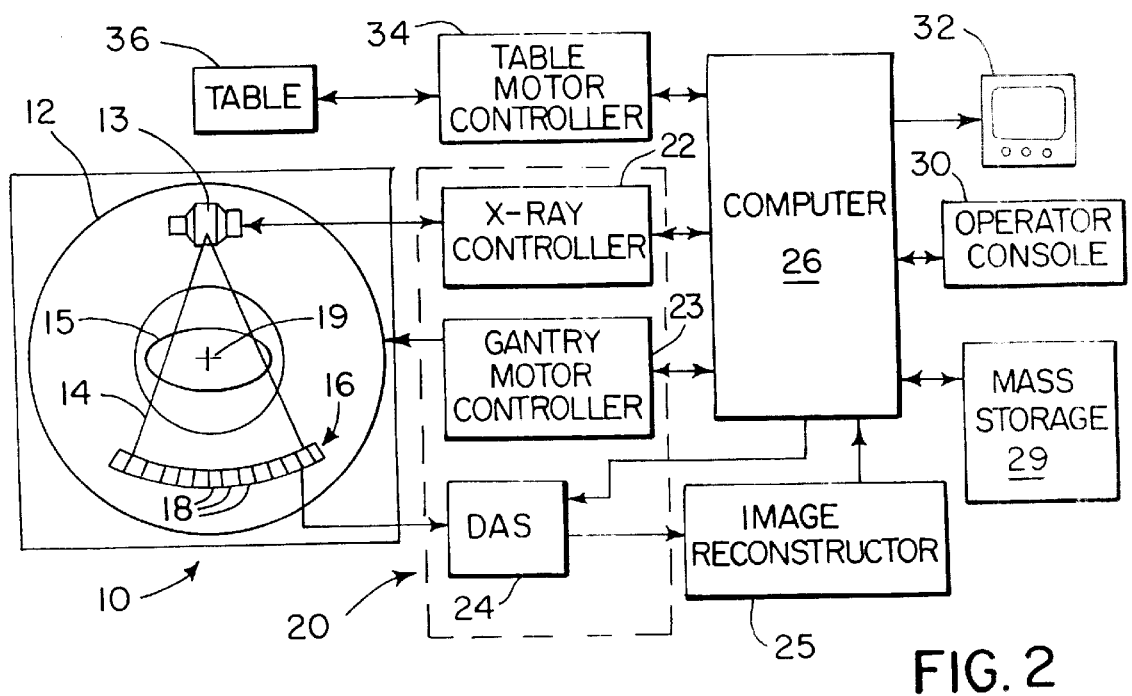
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Referring particularly to FIG. 3, the computer 26 includes a programmed CPU 50 and command sequencer indicated generally at 52. In response to the scan parameters input by the operator, the CPU 50 produces a series of commands which are output at 54 and stored in a command FIFO memory 56. As will be explained in more detail below, these commands control the operation of the x-ray controller 22 and the DAS 24 during the scan. The commands are performed by the command sequencer 52 during the scan, thus releasing the CPU 50 to perform other functions.

Commands stored in the FIFO memory 56 are read out one at a time in sequence and stored in a buffer memory 58. Each command remains in the buffer memory 58 during the duration of the command, and the data fields therein control the operation of the command sequencer 52 as will be described in more detail below. When a command is completed a next command control line 60 is enabled by control logic 62 to read out the next command from the FIFO memory 56 and store it in buffer memory 58. While an addressable memory device may be used to store the commands, a FIFO memory device is preferred because the next command in the series is automatically read out when the control line 60 is enabled without the need for producing an address.

Referring still to FIG. 3, a clock select field in each command is coupled from the buffer memory 58 to a clock source select circuit 64. A set of clock sources that may be used to perform different scans are input to the circuit 64 and the clock select field in the active command identifies one of them. The selected clock signal is output at 66 to a counter 68 and to a data acquisition clock gate 70.

The counter 68 is connected to receive a count field in the active command stored in buffer memory 58. The count field indicates the number of clock pulses required to complete the command. The counter 68 counts the number of clock pulses received from the circuit 64 and asserts a "count done" control line 72 when the indicated number of clock pulses have been received. This determines the duration of the active command in the buffer memory 58.

The clock select field and the count field may be used to control a variety of different functions. For example, when a "scout" scan is performed the gantry remains stationary and a conventional x-ray image is produced from a single projection angle. In this case a crystal clock source is selected by the clock select field and the count field is set to a count that will provide the prescribed exposure at the selected clock rate. On the other hand, during a CT scan, the gantry is rotated and a clock source driven by a shaft encoder coupled to the gantry is selected such that views are acquired at selected projection angles determined by the value in the count field.

The data acquisition clock gate 70 connects to receive a data acquisition enable bit from the buffer memory 58 through line 74. When this bit is set in the active command, the data acquisition clock gate applies the clock signal on line 66 to the DAS 24 through control line 76. For the duration of the active command, therefore, the selected clock signals are applied to the DAS 24 to sample the detected signals.

The operation of the x-ray controller 22 is controlled by an x-ray command field in the active command. This x-ray command drives an x-ray command control line 78 to either turn the x-ray source on or off during the duration of the active command.

The active command in the buffer memory 58 contains a repeat command field which is applied to a repeat select circuit 80. This multi-bit field indicates the number of times the active command is to be repeated. In the alternative, it may select one of a plurality of control lines 82 that indicate whether or not the active command is to be repeated. If the active command is to be repeated, this is signaled to control logic 62 through a repeat line 84 and the counter 68 is reset through control line 86.

The active command also contains a hold field which is applied to a hold select circuit 90. This multi-bit field selects one of a plurality of hold control lines 92 that may be asserted by external circuitry to halt the command sequencer 52. When the selected hold control line 92 is asserted, the signal is passed through a control line 94 to the control logic 62 to indicate that the currently active command is to be maintained in the buffer memory 58. When the hold control line 94 is released, the command sequencer 52 is allowed to continue to the next command.

An example of how the hold field and the repeat command field may be used is illustrated in a fluoroscopy application. During the procedure a foot pedal gives the operator control of when to acquire views. This foot pedal may be selected by the hold field to halt view acquisitions until the foot pedal is depressed and a view acquired, the repeat command field is set to repeat the view acquisition a preset number of times. This ensures that enough new views are acquired during each foot pedal depression to meaningfully update the data and reconstruct another image.

The control logic 62 receives the count done signal on the control line 72 and determines if the next command is to be transferred from the 15 command FIFO memory 56 to the buffer memory 58. If the hold control line 94 is asserted, the control logic 62 blocks the next command until the hold control line 94 is released. If the repeat control line 84 is asserted, the control logic 62 disregards the count done signal on line 72 and the command sequencer is allowed to repeat execution of the active command.

The elements of the command sequencer may be constructed using commercially available integrated circuits. Preferably, however, all the elements are contained in a single custom integrated circuit which serves as a peripheral device for the CPU 50. After the set of commands are downloaded by the CPU 50 to the command FIFO memory 56, the CPU 50 is free to perform other functions. The last command contains a single "done" bit, and this bit is set in the last command of the series. This done bit is applied to a gate 100 which also receives the signal on control line 60 indicating that the last active command has been performed. The gate 100 signals the CPU 50 that the scan is completed, or that another set of commands should be downloaded to the FIFO memory 56.

What is claimed is:

1. A command sequencer for a CT imaging system, the combination comprising:

a memory for storing a set of commands to be performed, each command containing an x-ray command field, a data acquisition command field and a count field;

logic means for sequentially reading each command stored in the memory;

means responsive to the x-ray command field in a command read from the memory for producing an x-ray command signal that indicates whether an x-ray source in the CT imaging system is to be energized or deenergized;

means responsive to the data acquisition command field in a command read from the memory for producing a data acquisition signal that indicates when data is to be acquired from a data acquisition system in the CT imaging system;

a clock source for producing a series of clock pulses;

a counter coupled to receive the count field in a command read from the memory and the series of clock pulses, and being operable to produce a count done signal to the logic means indicating the command has been performed when a number of clock pulses indicated by the count field have been produced; and the logic means is responsive to the count done signal to read the next command.

2. The command sequencer as recited in claim 1 in which the memory is a FIFO memory.

3. The command sequencer as recited in claim 1 which includes a buffer memory that stores each command read from the memory.

4. The command sequencer as recited in claim 1 in which the means responsive to the data acquisition command field includes a gate which employs the clock pulses to produce the data acquisition signal when the data acquisition command field indicates data is to be acquired.

5. The command sequencer as recited in claim 1 in which each command includes a clock select field and the command sequencer includes:

a clock source select circuit responsive to the clock select field in a command read from the memory and being operable to select the clock source from a plurality of available clock sources.

6. The command sequencer as recited in claim 1 in which each command includes a repeat select field and the command sequencer includes:

a repeat select circuit responsive to the repeat select field in a command read from the memory to produce a repeat signal for the logic means which causes the same command to be performed.

7. The command sequencer as recited in claim 1 in which the repeat select field indicates one of a plurality of available repeat signals and the repeat select circuit is operable to select one available repeat signal to produce the repeat signal.

8. The command sequencer as recited in claim 6 in which the repeat select circuit produces a signal that resets the counter.

9. The command sequencer as recited in claim 1 in which each command includes a hold select field and the command sequencer includes:

a hold select circuit responsive to the hold select field in a command read from the memory to produce a hold signal for the logic means which inhibits it from reading out a next command from the memory.

10. The command sequencer as recited in claim 9 in which the hold select field indicates one of a plurality of available hold signals and the hold select circuit is operable to select one available hold signal to produce the hold signal.

11. A command sequencer for a CT imaging system which comprises:

a command memory for storing a set of commands that control the operation of an x-ray source and the operation of a digital acquisition system during the performance of a scan;

a buffer memory for receiving a command read from the command memory;

means connected to the buffer memory for operating the x-ray source in response to an active command in the buffer memory;

means connected to the buffer memory for operating the data acquisition system in response to an active command in the buffer memory;

a clock for producing clock pulses;

a counter connected to receive a count contained in an active command in the buffer memory and the clock pulses, and being operable to indicate that the active command has been performed when the number of clock pulses indicated by the count have been received; and a logic circuit responsive to the indication from the counter to transfer the next command stored in the command memory to the buffer memory.

12. The command sequencer as recited in claim 11 in which the means for operating the data acquisition system includes a gate which couples clock pulses to the data acquisition system when data is to be acquired.

13. The command sequencer as recited in claim 11 which includes:

a clock source select circuit responsive to an active command in the buffer memory to select one of a plurality of available clock sources to produce the clock pulses.

14. The command sequencer as recited in claim 11 which includes:

a repeat circuit responsive to an active command in the buffer memory to produce a repeat signal which causes an active command in the buffer memory to be performed again.

15. The command sequencer as recited in claim 14 in which the counter is reset by the repeat circuit when the repeat signal is produced.

16. The command sequencer as recited in claim 11 which includes:

a hold circuit responsive to an active command in the buffer memory to produce a hold signal which inhibits the operation of the logic circuit.

* * * * *